United States Patent
Führer et al.

(10) Patent No.: US 6,642,415 B1
(45) Date of Patent: Nov. 4, 2003

(54) METHOD FOR RECOVERING FLUORINATED EMULSIFIERS

(75) Inventors: Stephan Führer, Kastl (DE); Klaus Hintzer, Kastl (DE); Gernot Löhr, Burgkirchen (DE); Werner Schwertfeger, Altötting (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/110,643

(22) PCT Filed: Oct. 28, 2000

(86) PCT No.: PCT/EP00/10638

§ 371 (c)(1),
(2), (4) Date: Apr. 12, 2002

(87) PCT Pub. No.: WO01/32563

PCT Pub. Date: May 10, 2001

(30) Foreign Application Priority Data

Nov. 5, 1999 (DE) .......................... 199 53 285

(51) Int. Cl.$^7$ .................. C07C 53/15; C07C 53/16; C07C 17/38
(52) U.S. Cl. ............ 562/602; 570/177; 570/178; 570/179; 570/180
(58) Field of Search .................. 562/602; 570/177, 570/178, 179, 180

(56) References Cited

U.S. PATENT DOCUMENTS 3,882,153 A    5/1975    Seki et al.

FOREIGN PATENT DOCUMENTS

| DE | 43 18 258 A | 8/1994 |
| DE | 199 32 771.8 | 7/1999 |
| EP | 0 014 431 B | 8/1980 |
| WO | WO 99/62830 | 12/1999 |
| WO | WO 99/62858 | 12/1999 |

OTHER PUBLICATIONS

*Encyclopedia of Polymer Science and Engineering*, John Wiley & Sons, 1985, vol. 8, p. 347.
*Encyclopedia of Chemical Technology*, Kirk–Othmer, John Wiley & Sons, 3$^{rd}$ Edition, 1978, vol. 13, p. 687.

Primary Examiner—Johann Richter
Assistant Examiner—Elvis O. Price
(74) Attorney, Agent, or Firm—James V. Lilly; Brian E. Szymanski

(57) ABSTRACT

Fluorinated emulsifiers, in particular, perfluorooctanoic acid are bound to anionic exchange resins for the purification of aqueous effluent from the production of fluoropolymers. Said emulsifiers may be quantitatively eluted from the exchanger with a water-miscible organic solvent, containing a small amount of ammonia. It is of advantage to distil off the ammonia containing solvent, recycle the emulsifier to a further polymerization and recycle the ammoniacal solvent for elution. Addition of alkalis improves the elution efficiency.

6 Claims, No Drawings

METHOD FOR RECOVERING FLUORINATED EMULSIFIERS

This application is a 371 national stage application of PCT International Application Serial No. PCT/EP00/10638 filed Oct. 28, 2000 (International Publication Number WO 01/32563, published May 10, 2001), which claims priority to German Application No. 199 53 285.0, filed Nov. 5, 1999.

The invention pertains to a method for eluting fluorinated emulsifiers from anion exchanger resins in a basic environment, which is especially useful for purifying aqueous effluent from the production of fluoropolymers.

Fluoropolymers such as fluoroelastomers, fluorothermoplastics and polytetrafluoroethylene (PTFE) are produced through aqueous radical emulsion polymerization. Emulsion polymerization requires highly fluorinated emulsifiers to ensure satisfactory colloidal stability. The emulsifiers used should not react with the fluoropolymer radicals, and therefore should not be telogenic. Usually used is APFOS, the ammonium salt of perfluorooctanoic acid (PFOS).

The polymerization is followed by the isolation of the polymer through coagulation of the polymer dispersion, either mechanically, at high shear speed, or chemically, by adding strong mineral acids such as HCl or $HNO_3$. The coagulated fluorothermoplastics are usually agglomerated by adding organic solvents that are usually not water-miscible, such as benzene or fluorinated hydrocarbons. The isolated polymer resins are washed with water. With 5 to 10 tons of water used for each ton of resin, relatively large amounts of process water, called aqueous effluent here, are generated. The aqueous effluent contains an average of 30 to 1000 ppm of PFOS. It is characteristic of the coagulation of fluoropolymers produced in the presence of fluorinated emulsifiers, that the emulsifier is desorbed to a great extent during coagulation, and a very large proportion of it is washed out. Thus, more than 80% of the fluorinated emulsifiers that are used get into the aqueous effluent. Along with latex particles, this aqueous effluent also contains the additives from the various polymerization formulas, such as buffers, initiators and various chain transmitters, for example, diethyl malonic ester and its decomposition products, alkyl chloride or alkane, benzene and other organic compounds from the processing.

The fluorinated emulsifier, APFOS in particular, is a very expensive compound and contributes very substantially to the overall cost of fluoropolymers from emulsion polymerization. As a result, its recovery is very important for economic reasons. In addition, fluorinated emulsifiers are practically non-degradable biologically, and injury to the health is suspected according to the most recent studies.

It is therefore desirable to remove the emulsifier from the aqueous effluent, to recover it and to recycle it to the emulsion polymerization. Removal from the aqueous effluent is preferably carried out using anion exchanger resins in accordance with U.S. Pat. No. 3,882,153 and EP-B-14 431. Other aqueous effluent treatments were suggested in this regard in WO-A-99/62858 and WO-A-99/62830. Both aqueous effluent treatments pertain to removal of PFOS from industrial aqueous effluents by means of anion exchangers, whereby strongly basic anion exchangers are recommended. The anionic exchange is hindered by the presence of fluoropolymer latex particles that clog the anion exchanger columns. According to WO-A-99/62858, the latex particles are precipitated through the addition of relatively large amounts of salt before the ionic exchange.

According to WO-A-99/62830, the fine latex particles are stabilized through the addition of nonionic tensides, thus preventing clogging of the anion exchanger columns, even during continuous operation.

Removal of the emulsifier from the aqueous effluent with an anion exchanger resin is very efficient. Particularly in the case of strongly basic anion exchanger resins, practically quantitative removal takes place. The emulsifier is selectively adsorbed, and thus the entire capacity of the ionic exchanger can be fully utilized.

However, the elution, termed recovery in the following, is made substantially more difficult in accordance with the strong adsorption. For example, the elution with solutions of 1 mol/liter each of $NH_3$, NaOH and KF of a strongly basic anion exchanger resin that is charged to breakdown with APFOS yields APFOS concentrations in the range of only 0.1 mmol/liter (40 ppm) in the eluate. Consequently, this method for recovering APFOS from larger volumes of aqueous effluent is not economically justifiable.

To elute for economically viable recirculation, an eluate peak concentration that is as high as possible is needed. According to EP-B-14 431, a peak concentration of 180,000 ppm with an eluent comprised of 89 wt.-% methanol, 4 wt.-% sulfuric acid and 7 wt.-% water can be achieved. The elution takes place in an acidic environment.

In a basic environment, according to U.S. Pat. No. 3,882,153 a relatively high peak concentration is achieved with an APFOS-charged, weakly basic anion exchanger during elution with 0.5 to 2 molar aqueous ammonia solution. However, the peak concentration of APFOS that can be achieved is smaller than in EP-B-14 431 by a factor of 2 to 3, and is still not satisfactory for a technically practicable process.

According to the unpublished German patent application 199 32 771.8 of Jul. 14, 1999, the elution of strongly basic anion exchanger resins in a basic environment runs substantially more efficiently in the presence of organic, water-miscible solvents. However, the peak concentration of 180,000 of EP-B-14 431 is achieved only with mixtures that are relatively laborious technically.

The object of the present invention is to make available a method in which fluorinated emulsifiers, PFOS in particular, can be recovered from anion exchanges with technically simple eluent mixtures with APFOS concentrations that are as high as possible.

It has now been found that with moderately and weakly basic anion exchanger resins, the PFOS concentrations in the eluate can be substantially increased with ammoniacal organic solvents. This eluate concentration is increased even further in the presence of alkali hydroxides.

The solution is a method for eluting fluorinated emulsifiers is made available in which weakly to moderately strong basic anion exchanger resins that are charged with fluorinated emulsifiers, particularly PFOS, are eluted with ammonia containing, water-miscible organic solvents.

According to the invention, the 180,000 ppm that can be achieved in the state of the art can be markedly surpassed, to beyond 300,000 ppm, for example, and specifically by using technically simple eluent mixtures.

The present invention makes possible significantly higher peak concentrations, thus considerably reducing the amount of highly flammable organic solvent needed for regenerating an anion exchanger resin.

Concentrated eluates of this type bring with them substantial advantages for the technical handling of the recovery. In addition, the recycling of PFOS becomes significantly easier, as will be explained in the following. The organic solvent, including the ammonia, is separated by means of distillation and is replaced with water as required.

The distillate mixture can be used for regenerating the ion exchanger directly. During distillation, the organic impurities from the aqueous effluent from the processing, such as chain transmitters or benzene, are removed from the eluate in a trouble-free manner during removal of the organic solvents, because the salts of PFOS are not volatile in water vapor.

The present invention represents a technical method for recovering PFOS from industrial aqueous effluents. Recycling in the sense of the present invention consists in making available the emulsifier, which is free of the impurities that enter during polymerization.

The ammonia concentration in the mixture is advantageously a minimum of 0.1 mol/liter and a maximum of 4 mol/liter, preferably 1 to 2.5 mol/liter. The ammonia concentration is advantageously produced by adding appropriate amounts of concentrated aqueous ammonia solutions, such as are commercially available, to the organic solvent. The system must contain an adequate amount of water so that the required anions can be released.

Suitable organic solvents are water-miscible, and should have a boiling point below 150° C., preferably below 110° C. "Miscible" is preferably to be understood in the sense of "infinitely miscible". Preferred solvents, which can be used individually or in a mixture, are alkanols with 1 to 4 carbon atoms, acetone, dialkyl ethers of monoglycol and diglycol, whereby alkyl groups are understood to mean methyl or ethyl. Especially preferred solvents are methanol, ethanol, n- and iso-propanol and dimethyl monoglycol ether. The essential cation is the ammonia ion. Addition of alkali hydroxides leads to higher eluate concentrations.

The definition of strongly, moderately and weakly basic anion exchangers can be found in the "Encyclopedia of Polymer Science and Engineering", John Wiley & Sons, 1985, Volume 8, page 347, and "Kirk-Othmer", John Wiley & Sons, 3rd Edition, Volume 13, page 687. Strongly basic anion exchangers typically contain quaternary amines, moderate strength tertiary amines and the weak secondary amines as functional exchange locations. The resin vendors classify the strength of the resins in the product description supplements.

Moderate strength anion exchangers are preferred because of their good effectiveness in removing APFOS from industrial aqueous effluents, especially in the presence of the nonionic emulsifiers described in German patent application 199 33 696.2 of Jul. 17, 1999.

In principle, this inventive method can be carried out with all fluorinated anionic emulsifiers. Essentially, this involves fluorinated alkanoic carboxylic and alkanoic sulfonic acids, whereby the alkyl residue is partly or preferably completely fluorinated and is generally linear or even branched.

Primarily to be understood here by the term fluorinated emulsifiers are perfluorinated alkanoic acids with the formula $CF_3(CF_2)_nCOOH$ (n=3 to 10), in particular PFOS, on which the method according to the invention can preferably be applied. Also covered by this term, however, are partially fluorinated alkanoic acids with the formula $XCF_2(CF_2)_nCOOH$ (X=H or Cl, n=3 to 10), perfluorinated or partially fluorinated alkanoic sulfonic acids with the formula $XCF_2(CF_2)_nSO_3H$ (X=H or preferably F, n=3 to 10), and perfluoro-[(β-propoxy)propionic acids]. The fluorinated emulsifier can also contain $[(CF_2)_nO]$ groups where $n \geq 2$. These fluorinated emulsifier acids can also be eluted according to the method per the invention. Mixtures of the named fluorinated emulsifier acids can also be adsorbed and eluted, particularly those that contain PFOS as a primary constituent.

EXAMPLES

Columns 30 cm long and 6.5 cm in diameter are filled with 200 to 240 ml of the medium strength ion exchanger Amberlite® IRA 67 or the weak anion exchanger Amberlite® IRA 92, both sold by Rohm & Haas GmbH, Germany. These exchanger resins are charged to breakdown with APFOS, available from 3M under the trade name FC® 8 143. The charged exchanger resins are washed with at least 5 times the bed volume of deionized water. The PFOS concentration in the final wash water is below 30 ppm. That is followed by elution with mixtures of methanol and a corresponding amount of 28 wt.-% aqueous ammonia solution at an elution speed of 100 ml/hour, in the comparison examples with 1 mol/liter of aqueous ammonia solution without methanol. The APFOS concentrations from each bed volume passed through are measured separately and are listed in Tables 1 through 4.

Comparison Example 1

Two hundred ml of the weakly basic anion exchanger Amberlite IRA 92 adsorbs 97 g APFOS. The wash water eluate of the charged ion exchanger comes to 5 ppm PFOS. The elution with 1 mol/liter aqueous ammonia solution shows a peak concentration of 76,000 ppm.

Comparison Example 2

Two hundred ml of the moderately basic anion exchanger Amberlite IRA 67 adsorbs 141 g APFOS. The wash water eluate of the charged ion exchanger has a PFOS concentration of 18 ppm. The peak concentration is 16,000 ppm.

TABLE 1

| Comparison Example 1 Amberlite IRA 92 (weakly basic) | | Comparison Example 2 Amberlite IRA 67 (moderately basic) | |
|---|---|---|---|
| Bed Volume | APFOS Concentration [ppm] | Bed Volume | APFOS Concentration [ppm] |
| 0.44 | 22,000 | 0.43 | 260 |
| 1.23 | 60,000 | 1.36 | 1,700 |
| 2.56 | 76,000 | 2.12 | 14,000 |
| 3.58 | 24,000 | 3.07 | 16,000 |
| 4.64 | 12,000 | 4.17 | 13,000 |

Example 1

The elution of 220 ml Amberlite IRA 67 takes place with 0.5 mol/liter $NH_3$ in methanol, produced from methanol and 28 wt.-% aqueous $NH_3$ solution. The APFOS concentration in the eluate is one multiple greater than in comparison example 2 without methanol. It is 140,000 ppm.

Example 2

Two hundred twenty ml Amberlite IRA 67 is quantitatively eluted with 5 bed volumes using 1 mol/liter $NH_3$, produced from methanol and 28 wt.-% aqueous $NH_3$ solution. The peak concentration is 250,000 ppm.

Example 3

Two hundred twenty ml Amberlite IRA 67 is quantitatively eluted with approximately 2 to 3 bed volumes using 2 mol/liter $NH_3$, produced from methanol and 28 wt.-% aqueous $NH_3$ solution. The peak concentration is 300,000 ppm.

TABLE 2

Example 1
0.5 mol/liter $NH_3$

| Bed Volume | APFOS Concentration [ppm] |
|---|---|
| 0.61 | 66 |
| 1.55 | 120,000 |
| 2.78 | 140,000 |
| 3.92 | 140,000 |
| 4.65 | 140,000 |

Example 2
1.0 mol/liter $NH_3$

| Bed Volume | APFOS Concentration [ppm] |
|---|---|
| 0.67 | 11,000 |
| 1.47 | 180,000 |
| 2.42 | 250,000 |
| 3.60 | 240,000 |
| 5.0 | 13,000 |

Example 3
2.0 mol/liter $NH_3$

| Bed Volume | APFOS Concentration [ppm] |
|---|---|
| 0.52 | 48,000 |
| 1.61 | 300,000 |
| 2.14 | 260,000 |
| 3.20 | 3,200 |
| 4.47 | 32 |

Example 4

Two hundred forty ml Amberlite IRA 67 is quantitatively eluted with approximately 2 to 3 bed volumes using a methanol solution containing 0.9 mol/liter aqueous $NH_3$, and 1.1 mol/liter NaOH, and showed a very high peak concentration of 340,000 ppm.

TABLE 3

| Bed Volume | APFOS Concentration [ppm] |
|---|---|
| 0.61 | 71,000 |
| 1.76 | 340,000 |
| 2.77 | 93,000 |
| 3.76 | 2,100 |
| 5.02 | 59 |

Example 5

Two hundred twenty ml Amberlite IRA 92 (weakly basic) is eluted with a pronounced maximum using 1.0 mol/liter $NH_3$, produced from methanol and 28 wt.-% aqueous $NH_3$ solution. The APFOS concentration in the eluate is one multiple greater than in comparison example 1 without methanol.

TABLE 4

| Bed Volume | APFOS Concentration [ppm] |
|---|---|
| 0.59 | 1,000 |
| 1.66 | 140,000 |
| 2.37 | 260,000 |
| 3.73 | 24,000 |
| 5.01 | 1,100 |

What is claimed is:

1. Method for recovering fluorinated emulsifiers from weakly to moderately basic anion exchange resins with (by using) at least one ammonia-containing and water-miscible organic solvent that has a boiling point below 150° C.

2. Method according to claim 1, characterized in that the emulsifier is a monovalent salt of a perfluoroalkanoic acid.

3. Method according to claim 1 or 2, characterized in that the solvent has a boiling point below 110° C.

4. Method according to claim 1 or 2, characterized in that the solvent is methanol.

5. Method according to claim 1, characterized in that the emulsifier is a perfluorooctanoic acid.

6. Method according to claim 1 or 2, characterized in that the emulsifier is eluted from the anion exchange resins and is recycled.

* * * * *

UNITED STATES PATENT AND TRADEMARK OFFICE
CERTIFICATE OF CORRECTION

PATENT NO. : 6,642,415 B1
DATED : November 4, 2003
INVENTOR(S) : Fuehrer, Stephan It is certified that error appears in the above-identified patent and that said Letters Patent is hereby corrected as shown below:

<u>Column 3,</u>
Line 62, "$n \geqq 2$" should be shown as -- $n \geq 2$ --

<u>Column 4,</u>
Lines 8-9, "FC® 8 143" should be shown as -- FC® 143 --

Signed and Sealed this

Twenty-seventh Day of April, 2004

JON W. DUDAS
*Acting Director of the United States Patent and Trademark Office*